United States Patent
Boesten et al.

(12)

(10) Patent No.: US 6,503,727 B1
(45) Date of Patent: *Jan. 7, 2003

(54) PROCESS FOR THE PREPARATION OF AN ANTIBIOTIC

(75) Inventors: Wilhelmus H. J. Boesten, Sittard (NL); Wilhelmus J. J. Van Den Tweel, Meerssen (NL); Rocus M. Dekkers, Barendrecht (NL)

(73) Assignee: Gist-Brocades, B.V., Delft (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/077,727
(22) PCT Filed: Dec. 6, 1996
(86) PCT No.: PCT/NL96/00479
§ 371 (c)(1), (2), (4) Date: Aug. 26, 1998
(87) PCT Pub. No.: WO97/22610
PCT Pub. Date: Jun. 26, 1997

(30) Foreign Application Priority Data

Dec. 8, 1995 (BE) .............................................. 9501015

(51) Int. Cl.[7] ........................... C12P 35/02; C12P 37/00
(52) U.S. Cl. .............................. 435/51; 435/43; 435/44; 435/45; 435/46; 435/47; 435/48; 435/49; 435/50; 435/147
(58) Field of Search .............................. 435/43, 44, 45, 435/46, 147, 47, 48, 49, 50, 51

(56) References Cited

U.S. PATENT DOCUMENTS 4,340,672 A * 7/1982 Kondo et al. .................. 435/45
5,874,571 A * 2/1999 Boesten et al. ............. 540/220

FOREIGN PATENT DOCUMENTS

| PL | 71240 | * | 4/1974 |
| WO | 92/01061 | * | 1/1992 |

OTHER PUBLICATIONS

Giacobbe et al., J. of Solid Phase Biochemistry, vol. 2, pp. 194–202, 1977.*

Ishimura et al. Kagaku Kogaku Ronbunshu (1994) 20(5): 657–65 (abstract only), 1994.*

El–Din et al. Acta Microbiol. Pol., Ser. B (1973) 5(1): 43–9 (abstract only), 1973.*

Nys et al. Antibiotiki (1976) 21(5)L 391–4 (abstract only), May 1976.*

* cited by examiner

*Primary Examiner*—Irene Marx
(74) *Attorney, Agent, or Firm*—Pillsbury Winthrop LLP

(57) ABSTRACT

The invention relates to a process for the preparation of an antibiotic, in particular cefalexin, ampicillin, amoxicillin, cefaclor, cefradin, cefadroxil, cefotaxim and the like, wherein a beta-lactam core is acylated, the antibiotic is recovered from the reaction mixture, the remaining mother liquor is subjected to a hydrolysis reaction in which the antibiotic present in the mother liquor is decomposed into its initial compounds, in particular the beta-lactam core, and the acylation agent is hydrolized. The beta-lactam core can then be recovered virtually quantitatively or recycled to the acylation reaction. This is because it has been found that the solubility of the beta-lactam core is unexpectedly high at relatively high concentrations of acylation agent and antibiotic.

18 Claims, No Drawings

PROCESS FOR THE PREPARATION OF AN ANTIBIOTIC

This application is a 371 of PCT NL 96/00479 filed Dec. 6, 1996.

The invention relates to a process for the preparation of an antibiotic wherein a β-lactam core is acylated and the antibiotic is recovered from the reaction mixture and subsequently the remaining mother liquor is worked up.

In the preparation of antibiotics involving the acylation of a β-lactam core with an acylation agent, for instance a derivative of a D-phenyl glycine, the recovery of the antibiotic and the working up of the reaction mixture are difficult in general. Thus WO-A-93/12250 for instance describes that the acylation reaction never runs to completion and the ultimate purification of the final product is hindered because the acid/base properties and solubilities of some other components that are present (in particular 7-ADCA and phenyl glycine in the case of cephalexin preparation as described in U.S. Pat. No. 4,003,896) differ little from those of the final product. As a result, coprecipitation occurs, so that impure antibiotic, i.c. cephalexin, is obtained. In WO-A-93/12250 and U.S. Pat. No. 4,003,896 the use of a complexing agent such as naphthol is proposed. However, this entails the drawback that an additional substance alien to the process has to be added.

The objective of the invention is to provide a simple, general and widely applicable process, enabling the antibiotic to be recovered pure, without using such organic compounds that are foreign to the process and without large losses of costly (starting) material, i.c. β-lactam core.

This is achieved according to the invention in that in the working-up step the mother liquor—which still contains a relatively high concentration of antibiotic—is subjected to a hydrolysis reaction and subsequently the β-lactam core is at least partially re-used for instance in an acylation reaction.

The acylation reaction can be effected either chemically or enzymatically. In the case of a chemical acylation and subsequent working up, racemisation will generally also result in the formation of a very small amount of acylation product with the wrong side chain enantiomer. If the acylation product in the mother liquor is recycled, strong accumulation of this side product may occur. The process according to the invention, with the acylation product and the acylation agent (side chain) being hydrolyzed again, offers the additional advantage of circumventing this problem.

The process according to the invention is preferably carried out in combination with an enzymatic acylation reaction. In the state-of-the-art processes a large excess of acylation agent has to be used in an enzymatic acylation reaction in order to ensure a high yield of antibiotic relative to β-lactam core. This entails the drawback that either large losses of acylation agent occur as a result of hydrolysis or that a large quantity of the reaction mixture (that which remains after recovery of the antibiotic in the solid state) has to be worked up.

The applicant now has found a process wherein the use of a large excess of acylation agent during the acylation reaction is obviated and wherein nevertheless the β-lactam core losses are limited, by subjecting the mother liquor to a hydrolysis reaction in which antibiotic still present in the mother liquor is decomposed into its initial compounds and the acylation agent is hydrolized as well, with the ability to subsequently recover or recycle the β-lactam core. The fact is that it has appeared that the process according to the invention enables a simple process to be realized, with no need for full conversion of the β-lactam core, while nevertheless only minor losses of β-lactam core occur.

Surprisingly, it has been found that the solubility of the β-lactam core is influenced by the presence of remaining acylation agent and antibiotic in the reaction mixture, in the sense that the solubility of the β-lactam core is unexpectedly high at relatively high concentrations of acylation agent and antibiotic. As a result, it was found to be possible to recover virtually quantitatively the β-lactam core in the solid state by hydrolizing the mother liquor obtained after isolation of the antibiotic, which results in hydrolysis of the antibiotic and the acylation agent. Moreover, it was found that the β-lactam core, in the solid state, was recovered in a purer form than in a process in which hydrolysis of th)e mother liquor had not been effected. Especially the content of α-substituted acetic acid in the β-lactam core appeared to have been strongly decreased, which in turn had a surprisingly large effect on the acylation reaction speed. In particular, the content of phenylacetic acid in 7-ADCA and the content of phenyl or phenyloxy acetic acid in 6-APA appeared to be strongly decreased. In addition it appeared that the β-lactam core crystals contained little adhering moisture, which means a little amount of impurities. An additional advantage appears in that, because of their low solubility, the β-lactam core crystals could also be washed without large losses. This in turn, means a lower build-up of impurities, possibly accumulating in the antibiotic, in recycling.

The β-lactam core obtained after the hydrolysis reaction constitutes a novel composition that has particular advantages in the enzymatic preparation of β-lactam antibiotics. Applicant has found that the free phenyl or phenoxy acetic acid content in the β-lactam core recovered after hydrolysis, is significantly lower than that of the β-lactam core starting material, in particular it has appeared in relation to the 7-ADCA β-lactam core that where the free phenylacetic acid content of the 7-ADCA starting material was 120 ppm, the free phenylacetic acid content of the 7-ADCA obtained after hydrolysis was 69 ppm; for 6-APA these figures were 30 ppm and <15 ppm, respectively (ppm calculated with respect to the amount of β-lactam core). The invention, therefore, also relates to 7-ADCA with less than 100, in particular less than 80, preferably less than 70 ppm phenylacetic acid, and to 6-APA with less 20, preferably less than 15 ppm α-aryl- or aryloxy acetic acid, particularly α-phenyl- or α-phenyoxyacetic acid.

Another advantage of the process according to the invention is that as a rule the—generally valuable—hydrolized acylation agent can effectively be recovered.

Optionally, the β-lactam core can be recycled in solution to the acylation reaction after the hydrolysis reaction. Preferably, the β-lactam core is recovered, however, for instance by lowering the pH and isolating the β-lactam core precipitated in the solid state. The hydrolized acylation agent can be recovered at various places in the process as a whole, for instance after the hydrolysis reaction, after the recovery of the β-lactam core or after the condensation reaction.

The hydrolysis is preferably carried out in the presence of a suitable enzyme. Suitable enzymes for the enzymatic hydrolysis reaction are for instance the enzymes that are used in the preparation of β-lactam cores and in the enzymatic acylation reactions, for instance amidases or acylases, in particular penicillin amidases or acylases. Such enzymes are described for instance by J. G. Shewale et al. in Process Biochemistry, August 1989, pp. 146–154, and in Process Biochemistry International, June 1990, pp. 97–103. Examples of suitable enzymes are enzymes derived from Acetobacter, in particular *Acetobacter pasteurianum*, Aeromones, Alcaligenes, in particular *Alcaligenes faecalis,* Aphanocladium, Bacillus sp., in particular *Bacillus megaterium,* Cephalosporium, Escherichia, in particular *Escherichia coli,* Flavobacterium, Kluyvera, Mycoplana, Protaminobacter, Pseudomonas en Xanthomonas, in particular *Xanthomonas citril.*

Preferably an immobilized enzyme is used, since the enzyme can be easily isolated and re-used then. A suitable immobilization technology is described for instance in EP-A-222462. Another suitable technology consists in immobilizing the Penicillin G acylase on a carrier which contains a gelating agent, for instance gelatin, and a polymer with free amino groups, for instance alginate amine, chitosan or polyethylene imine. If besides the immobilized enzyme other solid substances are present as well, isolation can be effected with good results for instance by the method described in WO-A-9212782. Immobilized enzymes are known as such and are commercially available.

A suitable enzyme for the enzymatic hydrolysis reaction has appeared to be Penicillin-G acylase from *Bacillus megaterium* or *Alcaligenes faecalis,* described for instance in EP-A-453047. Also suitable are the *Escherichia coli* enzyme from Boehringer Mannheim GmbH, which is commercially available under the name 'Enzygel®', a Penicillin-G acylase from *Escherichia coli,* immobilized by means of the above-mentioned techniques, and the immobilized Penicillin-G acylase from Recordati.

A suitable method of recovering the antibiotic is for instance to lower the pH of the reaction mixture obtained after the acylation reaction, having a pH between 5 and 10, particularly between 6 and 10, preferably between 6 and 9, particularly between 7 and 8.5, thereby causing selective precipitation of the antibiotic; optionally, first the pH of the reaction mixture is brought to a value between 5 and 10, particularly between 6 and 10, preferably between 6 and 9 particularly between 7 and 8.5, and/or the solids are removed.

The optimum pH at which antibiotic is recovered depends on the composition of the mixture and is chosen such that optimum separation of β-lactam core and antibiotic is achieved. In practice the optimum pH is a compromise between on the one hand high purity of the antibiotic recovered, which is achieved if the antibiotic is recovered at a relatively high pH, so that the antibiotic is still partly in solution and the β-lactam core still completely in solution, and on the other hand a high yield, which is achieved if the pH at which the antibiotic is recovered is relatively low, so that the antibiotic has been precipitated virtually completely, while at the same time part of the β-lactam core has also been precipitated. For the person skilled in the art it is easy to determine the optimum pH in a given situation.

The pH may be lowered in several ways in the framework of the invention, for instance this may be done chemically by adding an acid, for instance a mineral acid or a carboxylic acid, in particular sulphuric acid, hydrochloric acid, nitric acid, acetic acid or formic acid. Another possibility can be applied where for instance, if D-phenyl glycine amide (PGA) has been used as acylation agent in the acylation reaction or if an ester of D-phenyl glycine (PGM) has been used and the pH has been kept constant by means of titration with ammonia during the acylation reaction. In such case the pH can be lowered through physical removal of ammonia. Suitable physical removal methods include for instance stripping with steam or an inert gas; (steam) distillation at reduced pressure, in particular thin-film evaporation; evaporation in a spray tower; gas membrane separation or electrodialysis.

The temperature at which the hydrolysis reaction is carried out is not particularly critical and is preferably between 0 and 50° C., in particular between 5 and 40° C., preferably between 15 and 30° C.

The pH at which the hydrolysis reaction is carried out is not particularly critical and is preferably between 6 and 9, in particular between 7 and 8.

The process according to the invention can be suitably applied for the preparation of β-lactam antibiotics, for instance cefalexin, amoxicillin, ampicillin, cefaclor, cefradin, cefadroxil and cefotaxim, cefazolin and the like.

Suitable examples of β-lactam cores which can be used according to the invention are various penicillanic acid derivatives, for instance 6-aminopenicillanic acid (6-APA), and cephalosporanic acid derivatives, for instance 7-aminocephalosporanic acid, with or without a substituent at the 3-site (7-ACA), for instance 7-aminodesacetoxycephalosporanic acid (7-ADCA) and 7-amino-3-chlorocephalosporanic acid (7-ACCA).

In the (enzymatic) acylation reaction, the acylation agent can be for instance a phenyl glycine in activated form, preferably an amide or an ester, for instance a methyl ester; suitable phenyl glycines are for instance substituted or non-substituted phenyl glycines, in particular phenyl glycine, p-hydroxyphenyl glycine, dihydrophenyl glycine.

The enzymatic acylation reaction is mostly carried out at a temperature lower than 40° C., preferably between 0 and 35° C. The pH at which the enzymatic acylation reaction is carried out is mostly between 5 and 10, particularly between 6 and 10, preferably between 6 and 9, particularly between 6.5 and 9.

In practice the (enzymatic) acylation reaction and the further working up of the reaction mixture are mostly carried out in water. Optionally, the reaction mixture may also contain an organic solvent or a mixture of organic solvents, preferably less than 30 vol. %. Examples of organic solvents that can be used are alcohols with 1–7 carbon atoms, for instance a monoalcohol, in particular methanol or ethanol; a diol, in particular ethylene glycol or a triol, in particular glycerol.

An embodiment of the process according to the invention is worked out in detail in the following, relating to the preparation of cephalexin from 7-ADCA and D-phenyl glycine amide (PGA). In this embodiment a reaction mixture obtained after an enzymatic acylation reaction at a pH between 8 and 10 and containing cephalexin, 7-ADCA, PGA and D-phenyl glycine (PG), is treated to isolate the solid it contains, which solid mainly consists of the immobilized enzyme and possibly PG. The pH of the remaining liquid mixture is then lowered to 6–8, particularly to 6.5–7.5, resulting in the formation of a precipitate which mainly contains cephalexin, after which the solid cephalexin is recovered. In this preferred embodiment the then remaining liquid mixture is subjected to an enzymatic hydrolysis, resulting in hydrolysis in particular of the remaining, dissolved cephalexin and the remaining PGA to 7-ADCA and PG and to PG, respectively; the PG precipitates virtually completely and can be isolated, for instance by filtration. It so desired the PG can be removed (in whole or partly) already during the hydrolysis reaction by circulation of the supsension over a filter outside the reactor. Next, the 7-ADCA can be separated from the then remaining mixture for instance after a further lowering of the pH, thereby causing the 7-ADCA to precipitate; it can then be isolated, for instance by filtration or centrifugation, and used again in an acylation reaction.

In the framework of the present invention the various components may be present in the reaction mixture in the free form or as salts. The pH values mentioned are in all cases the pH values measured with a pH electrode calibrated at room temperature.

The invention will be further elucidated by means of the following examples, without however being restricted thereto.

Abbreviations

| | |
|---|---|
| AMOX | = amoxicillin trihydrate |
| AMPI | = ampicillin trihydrate |
| CEX | = cephalexin |
| CEX.H$_2$O | = cephalexin monohydrate |
| 6-APA | = 6-aminopenicillanic acid |
| 7-ADCA | = 7-aminodesacetoxycephalosporanic acid |
| PGA | = D-phenyl glycine amide |
| PG | = D-phenyl glycine |
| HPGA | = D-p-hydroxyphenyl glycine amide |
| HPG | = D-p-hydroxyphenyl glycine |
| HPG-Me | = D-p-hydroxyphenyl glycine methyl ester |

EXAMPLE I
Effect of PGA and PEX on the Solubility of 7-ADCA

The following synthetic mixtures were prepared, with a final pH of 4.5;

Mixture 1:
  3% (m/m) 7-ADCA in water
Mixture 2:
  3% (m/m) 7-ADCA and 0.4% (m/m) PG in water
Mixture 3:
  3% (m/m) 7-ADCA, 0.4% (m/m) PG and 1.5% (m/m) PGA in water
Mixture 4:
  3% (m/m) 7-ADCA, 0.4% (m/m) PC, 1.5% (m/m) PGA and 3.0% (m/m) CEX.H$_2$O in water
Mixture 5:
  3% (m/m) 7-ADCA and 3.0% (m/m) CEX.H$_2$O in water.

After 2 hours' incubation in a shaker incubator (20° C.) samples were taken and the dissolved concentration of each of these components was determined.

| Result | Dissolved concentrations [% (m/m)] | | | |
|---|---|---|---|---|
| Mixture | PG | ADCA | PGA | CEX |
| 1 | — | 0.03 | — | — |
| 2 | 0.40 | 0.03 | — | — |
| 3 | 0.40 | 0.03 | 1.5 | — |
| 4 | 0.40 | 0.13 | 1.5 | 2.0 |
| 5 | — | 0.03 | — | 2.0 |

This table shows that only the combination of PG, PGA and CEX has any significant effect on the solubility of 7-ADCA.

EXAMPLE II
Effect of PQA and AMPI on the Solubility of 6-APA

The following synthetic mixtures were prepared, with a final pH of 4.5:

Mixture 1:
  3% (m/m) 6-APA in water
Mixture 2:
  3% (m/m) 6-APA and 0.4% (m/m) PG in water
Mixture 3:
  3% (m/m) 6-APA, 0.4% (m/m) PG and 1.5% (m/m) PGA in water
Mixture 4:
  3% (m/m) 6-APA, 0.4% (m/m) PG, 1.5% (m/m) PGA and 3.0% (m/m) AMPI in water After 2 hours' incubation in a shaker incubator (20° C.) samples were taken and the dissolved concentration of each of these components was determined. Results:

| | PG | 6-APA | PGA | AMPI |
|---|---|---|---|---|
| Mixture 1 | — | 0.35 | — | — |
| Mixture 2 | 0.4 | 0.40 | — | — |
| Mixture 3 | 0.4 | 0.40 | 1.5 | — |
| Mixture 4 | 0.4 | 0.90 | 1.5 | 0.7 |

Here only mixture 4 shows any significant effect on the solubility of 6-APA.

EXAMPLE III
Effect of HPGA/HPG-Me and AMOX on the Solubility of 6-APA

The following synthetic mixtures were prepared, with a final pH of 4.5:

Mixture 1:
  3% (m/m) 6-APA in water
Mixture 2:
  3% (m/m) 6-APA and 0.5% (m/m) HPG in water
Mixture 3:
  3% (m/m) 6-APA, 0.5% (m/m) HPG and 1.5% (m/m) HPGA in water
Mixture 4:
  3% (m/m) 6-APA, 0.5% (m/m) HPG and 2.0% HPG-Me in water
Mixture 5:
  3% (m/m) 6-APA, 0.5% (m/m) HPG, 1.5% (m/m) HPGA and 3.0% AMOX in water
Mixture 6:
  3.0% (m/m) 6-APA, 0.5% (m/m) HPG, 2.0% (m/m) HPG-Me and 3.0% (m/m) AMOX in water After 2 hours' incubation in a shaker incubator (20° C.) samples were taken and the dissolved concentration of each of these components was determined.

| Result | Dissolved Concentrations [% (m/m)] | | | | |
|---|---|---|---|---|---|
| Mixture | HPG | HPGA | 6-APA | KPG-Me | AMOX |
| 1 | — | — | 0.35 | — | — |
| 2 | 0.5 | — | 0.35 | — | — |
| 3 | 0.5 | 1.5 | 0.40 | — | — |
| 4 | 0.5 | — | 0.50 | 2.0 | — |
| 5 | 0.5 | 1.5 | 1.40 | — | 0.8 |
| 6 | 0.5 | — | 2.15 | 2.0 | 0.8 |

Here only mixtures 5 and 6 had any significant effect on the solubility of 6-APA.

Comparative Experiment A
Recovery of 7-ADCA from CEX Mother Liquor Through Acidification 1850 g of slurry containing 12.0% (m/m) of 7-ADCA and 7.2% (m/m) of POA was supplied to a sieve bottom reactor (pore size 40 μm) which contained 150 g of Enzygel®. The content of phenyl acetic acid in the 7-ADCA amounted to 120 ppm. The initial pH was 7.8 and the temperature was kept at 5° C. (reactor flushed continuously with N$_2$, stirring rate 500 r.p.m.).

After 3 hours' incubation the reaction mixture (final pH 8.4) was separated across the sieve bottom and the enzyme remaining behind was washed with 185 g of water.

Combining of the two flows resulted in a clear solution which contained 11.5% CEX.$H_2O$, 4.5% 7-ADCA, 1.5% PGA and 0.6% PG. Next, CEX.$H_2O$ was recovered through selective crystallization. To that effect $H_2SO_4$ (25% (m/m)) and said solution were supplied simultaneously to a crystallization vessel (pH 7.0, 30° C.). After recrystallization for 30 minutes the CEX.$H_2O$ crystals were separated by means of a centrifuge and washed with water and then an acetone/water (80:20) mixture. After drying 168 g of CEX.$H_2O$ was thus obtained. The mother liquor solution together with the CEX.$H_2O$ washing water had the following composition: CEX.$H_2O$ 2.64 (m/m), 7-ADCA 4.2% (m/m), PGA 1.4% (m/m), PC 0.5% (m/m).

When this solution was acidified further to pH 4.5, again using 25% $H_2SO_4$, a large portion of the valuable β-lactam components could be crystallized, isolated and recycled. The resulting mother liquor had the following composition: 1.8% (m/m) CEX.$H_2O$, 0.28% (m/m) 7-ADCA, 1.4% (m/m) PGA and 0.5% (m/m) PG.

EXAMPLE IV

Recovery of 7-ADCA from CRX Mother Liquor by Enzymatic Hydrolysis of the CEX Mother Liquor, Followed by Acidification The CEX.$H_2O$ mother liquor together with the CEX.$H_2O$ washing water (obtained as described in comparative experiment A) was brought to a pH of 7.6 with $NH_4OH$ and a temperature of 30° C. This solution was then supplied to a sieve bottom reactor (pore size 40 μm) containing 200 g of immobilized Penicillin-G acylase from Recordati. After reacting for 3 hours (500 r.p.m.) the reaction mixture, containing PG in solid form, was drained off and the enzyme and PG in solid form were washed with water in order to reduce β-lactam losses. When the two solutions had been combined the PC crystals were isolated by filtration. The resulting filtrate had the following composition: 4.2% (m/m) 7-ADCA, 0.04% (m/m) CEX.$H_2O$, 0.01% (m/m) PGA and 0.54% (m/m) PG.

This mother liquor was acidified with $H_2SO_4$ (25%) to pH 4.5, causing 7-ADCA to crystallize. After isolation of the 7-ADCA crystals by means of a centrifuge, a mother liquor with a very low β-lactam content was obtained: 0.04% (m/m) CEX.$H_2O$ and 0.08% (m/m) 7-ADCA.

The content of phenylacetic acid in the 7-ADCA obtained was 69 ppm.

EXAMPLE V

Use of the 7-ADCA obtained after a hydrolysis reaction, in an enzymatic acylation reaction.

The acylation reaction was carried out in the same way as in Example IV (or Comparative experiment A), apart from the fact that one half of the 7-ADCA used is the same as in Example IV and the other half consists of 7-ADCA which is regained after the hydrolysis of Example IV, and the fact that the incubation time was 2 hours. Essentially the same composition of the resulting process flows and the same yield of cephalexin were obtained.

What is claimed is:

1. A process for preparing a β-lactam antibiotic and forming a cephalosporanic or penicillanic acid, comprising:
   (i) preparing a β-lactam antibiotic by acylating, in a reaction mixture,
      (a) a cephalosporanic or penicillanic acid compound selected from the group consisting of 6-amino-penicillanic acid, 7-amino-cephalosporanic acid, 7-amino-desacetoxy-cephalosporanic acid, and 7-amino-3-chloro-cephalosporanic acid with
      (b) an acylating agent;
   (ii) removing a portion of the β-lactam antibiotic prepared in step (i) from said reaction mixture; and
   (iii) re-forming an amount of the cephalosporanic or penicillanic acid compound by hydrolyzing
      (a) β-lactam antibiotic remaining in the reaction mixture after step (ii) with
      (b) a hydrolyzing enzyme; and
   (iv) recovering the re-formed cephalosporanic or penicillanic acid compound from said reaction mixture.

2. The process according to claim 1 wherein said hydrolyzing enzyme is obtained from a microorganism selected from the group consisting of *Alcaligenes faecalis, Escherichia coli, Bacillus megaterium* and *Xanthomonas citri.*

3. The process of claim 1 wherein said hydrolyzing enzyme is in immobilized form.

4. The process of claim 1 wherein said hydrolyzing is effected at a pH of 6 to 8.5.

5. The process of claim 1 wherein said hydrolyzing is effected at a pH of 7 to 8.

6. The process of claim 1 wherein said portion of the β-lactam antibiotic is removed from said reaction mixture by a process comprising lowering the pH of said reaction mixture.

7. The process of claim 6, wherein said pH is modified by adding an acid to said reaction mixture.

8. The process of claim 1 wherein said β-lactam antibiotic is cefalexin formed by acylation of 7-aminodesacetoxy-cephalosporanic acid with D-phenyl glycine amide or an ester of D-phenyl glycine.

9. The process of claim 1 wherein said β-lactam antibiotic is amoxicillin formed by acylation of 6-amino-penicillanic acid with D-p-hydroxyphenyl glycine amide or an ester of D-p-hydroxyphenyl glycine.

10. The process of claim 1 wherein said β-lactam antibiotic is ampicillin formed by acylation of 6-amino-penicillanic acid with D-phenyl glycine amide or an ester of D-phenyl glycine.

11. The process of claim 1 wherein said β-lactam antibiotic is cefachlor formed by acylation of 7-amino-3-chloro-cephalosporanic acid with D-phenyl glycine or an ester of D-phenyl glycine.

12. The process of claim 1 wherein said β-lactam antibiotic is cefradin prepared by acylation of 7-amino-desacetoxy-cephalosporanic acid with D-dihydrophenyl glycine amide or an ester of D-dihydrophenyl glycine.

13. The process of claim 1 wherein said β-lactam antibiotic is cefadroxil formed by acylation of 7-amino-desacetoxy-cephalosporanic acid with D-p-hydroxphenyl glycine amide or an ester of D-p-hydroxyphenyl glycine.

14. The process of claim 1, comprising enzymatically acylating said acid compound in step (i).

15. The process of claim 1, further comprising modifying the pH of said reaction mixture after said hydrolyzing to precipitate the re-formed acid compound.

16. The process of claim 15, wherein said pH is modified by adding an acid to said reaction mixture.

17. The process of claim 1, wherein said reaction mixture comprises an organic solvent.

18. The process of claim 1, wherein said cephalosporanic or penicillanic acid compound is 6-amino-penicillanic acid.

* * * * *